(12) United States Patent
Cooke et al.

(10) Patent No.: US 10,401,323 B2
(45) Date of Patent: Sep. 3, 2019

(54) METHOD AND APPARATUS FOR PERFORMING ELECTROPHORESIS

(71) Applicant: UNIVERSITY OF LEICESTER, Leicester, Leicesterhire (GB)

(72) Inventors: Marcus Cooke, Leicester (GB); Mahsa Karbaschi, Leicester (GB)

(73) Assignee: UNIVERSITY OF LEICESTER, Leicester, Leicestershire (GB)

( * ) Notice: Subject to any disclaimer, the term of this patent is extended or adjusted under 35 U.S.C. 154(b) by 380 days.

(21) Appl. No.: 14/912,736

(22) PCT Filed: May 13, 2014

(86) PCT No.: PCT/GB2014/051459
§ 371 (c)(1),
(2) Date: Feb. 18, 2016

(87) PCT Pub. No.: WO2015/025123
PCT Pub. Date: Feb. 26, 2015

(65) Prior Publication Data
US 2016/0195494 A1    Jul. 7, 2016

(30) Foreign Application Priority Data
Aug. 22, 2013 (GB) .................................. 1315011.5

(51) Int. Cl.
*G01N 27/447* (2006.01)
*G01N 27/453* (2006.01)

(52) U.S. Cl.
CPC . *G01N 27/44756* (2013.01); *G01N 27/44743* (2013.01); *G01N 27/453* (2013.01)

(58) Field of Classification Search
CPC ........... G01N 27/44756; G01N 27/453; G01N 27/44743; G01N 27/447; G01N 27/26;
(Continued)

(56) References Cited

U.S. PATENT DOCUMENTS 3,856,655 A    12/1974  Roberts
5,350,069 A     9/1994  Agwu
(Continued)

FOREIGN PATENT DOCUMENTS

EP    2587257        5/2013
WO    02/21116 A2    3/2002

OTHER PUBLICATIONS

International Search Report in PCT/GB2014/051459, dated Jul. 20, 2014.
(Continued)

*Primary Examiner* — Gurpreet Kaur
(74) *Attorney, Agent, or Firm* — Florek & Endres PLLC

(57) ABSTRACT

This invention relates to a method of performing electrophoretic analysis on an substrate comprising: providing a substrate on a surface of at least one supporting member; and performing electrophoresis on the substrate by submerging the or each supporting member in an electrophoresis tank having a base and side walls enclosing a volume containing an electrophoresis buffer and inducing an electric current between ends thereof; wherein the or each supporting member is aligned within the tank such that each surface upon which the substrate is located is nonparallel with respect to the base of the electrophoresis tank and is substantially parallel with the direction of the electric current.

19 Claims, 5 Drawing Sheets

(58) Field of Classification Search
CPC ........ G01N 27/44769; B29C 39/00–06; B29C 39/22–26
USPC ....... 204/456, 466, 467, 457, 461, 462, 463, 204/464, 465, 606–609, 613, 615, 616, 204/617, 618
See application file for complete search history.

(56) References Cited

U.S. PATENT DOCUMENTS

| | | |
|---|---|---|
| 5,632,877 A | 5/1997 | Van Atta |
| 2004/0050699 A1* | 3/2004 | Goncalves ....... G01N 27/44704 204/450 |
| 2005/0103628 A1* | 5/2005 | Jackson ........... G01N 27/44704 204/456 |
| 2011/0042213 A1 | 2/2011 | Updyke et al. |
| 2013/0105320 A1* | 5/2013 | Samson ........... G01N 27/44756 204/461 |

OTHER PUBLICATIONS

Nickitas-Etienne, Athina, "International Preliminary Report on Patentability for PCT/GB2014/051459," International Bureau of WIPO, dated Feb. 23, 2016.
Dixon, Laura, "Examination Report under Section 18.3 for GB Patent Application No. 1602628.8," United Kingdom Intellectual Property Office, dated Aug. 31, 2018.

* cited by examiner

METHOD AND APPARATUS FOR PERFORMING ELECTROPHORESIS

This application is a U.S. National Stage filing under 35 U.S.C. § 371 of International Application No. PCT/GB2014/051459, filed May 13, 2014, which in turn claims priority to Great Britain Application No. 1315011.5, filed Aug. 22, 2013.

TECHNICAL FIELD OF THE INVENTION

The present invention relates to a method and apparatus for performing electrophoresis, and in particular, to a method and apparatus for performing single cell gel electrophoresis.

BACKGROUND TO THE INVENTION

Electrophoresis is a process used for the separation and characterisation of materials, such as DNA, RNA and proteins using the property that charged particles migrate in the presence of an electric field. Electrophoresis is widely used in a variety of fields including forensic science, molecular biology, genetics, microbiology and biochemistry.

Frequently, electrophoresis involves the separation of molecules within a gel matrix which is typically agarose, polyacrylamide or starch. The gel matrix acts to resolve the molecules based upon size as differently sized molecules move through the gel matrix at different rates. The gel matrix also acts to maintain the finished separation such that it can be analysed at a later point in time.

Single cell gel electrophoresis, sometimes known as the "comet assay", is a process by which DNA damage may be quantified in individual cells. The process may be run in neutral conditions where strand breaks in the DNA may be identified, and under alkaline conditions where alkali-labile sites or certain nucleobase modifications may also be identified. The principle of single cell gel electrophoresis is that strand breaks lead to a relaxation and unwinding of DNA under alkaline conditions. By subsequently applying an electric field, the DNA undergoes electrophoresis, that is, moving under the influence of the electric field which forms a 'comet shape' when viewed under a microscope. The amount of DNA in the comet 'tail' relative to the amount remaining in the comet 'head', is proportional to the number of strand breaks present. This provides a quantified measure of the DNA damage present in the cell of interest.

Single cell gel electrophoresis is conducted in a number of stages. In a typical procedure, the cell of interest is first embedded in low-melting agarose and then loaded onto a microscope slide which has been pre-coated with an agarose gel matrix. The gel is then subjected to a number of pre-electrophoresis steps including treatment at a high pH to lyse the cells and treatment with DNA repair enzymes. The slides are then transferred individually into an electrophoresis tank and electrophoresed. Following this, a number of post-electrophoresis steps are performed which may include neutralisation, washing, staining and drying. Finally, the cells are subjected to an imaging or scoring stage for analysis.

The multiple pre-electrophoresis and post-electrophoresis steps require the manipulation of multiple slides. In currently employed methods, the slides are manipulated individually through these steps, making the process laborious and time-consuming. Moreover, individual manipulation of slides presents an increased risk that the gels may become damaged, contaminated or lost.

Furthermore, the comet assay is conventionally performed with the microscope slides lying flat in the electrophoresis tank. A significant limitation to this convention is that placing microscope slides flat within the electrophoresis tank reduces the number of slides that can be contained within the tank at any one time, thus limiting the number of samples which can be electrophoresed in parallel.

It would therefore be advantageous to provide a method and/or apparatus for performing electrophoresis whereby each slide is not subjected to individual manipulation in a majority of steps of the process.

It would also be advantageous to provide a method and/or apparatus for performing electrophoresis which increases the throughput of the process.

It is an aim of embodiments of the invention to overcome or mitigate at least one of the problems of the prior art described above.

SUMMARY OF THE INVENTION

According to a first aspect of the present invention there is provided a method of performing electrophoretic analysis on a substrate comprising: providing a substrate on a surface of at least one supporting member; and performing electrophoresis on the substrate by submerging the or each supporting member in an electrophoresis tank having a base and side walls enclosing a volume containing an electrophoresis buffer and inducing an electric current between ends thereof; wherein the or each supporting member is aligned within the tank such that each surface upon which the substrate is located is nonparallel with respect to the base of the electrophoresis tank and is substantially parallel with the direction of the electric current.

The method may comprise aligning the or each supporting member such that the surface of the or each supporting member is substantially perpendicular to the base of the electrophoresis tank.

The method may further comprise providing a holder and placing the or each supporting member in the holder in order to retain each supporting member in the correct alignment with respect to the electrophoresis tank. In such embodiments the method may comprise placing the or each supporting member within a holder which is removable from within the electrophoresis tank.

The method may comprise performing electrophoretic analysis on a substrate located on a plurality of supporting members.

The holder may comprise a plurality of compartments for holding a plurality of supporting members.

The method may comprise performing electrophoretic analysis on any suitable substrate which may include DNA, RNA or proteins, for example.

The method may comprise performing any type of electrophoresis. In preferred embodiments the method comprises performing single cell gel electrophoresis.

The method may further comprise performing pre-electrophoresis processing steps prior to performing electrophoresis on the substrate.

In embodiments wherein the substrate comprises a single cell, such as in embodiments wherein the electrophoretic analysis comprises single cell gel electrophoresis, the pre-electrophoresis steps may include treating the substrate at a high pH to lyse the cell.

The method may further comprise performing post-electrophoresis processing steps after performing electrophoresis on the substrate. In such embodiments the post-electrophoresis steps may include any one or more of neutralisation of the substrate, washing the substrate, staining the substrate and drying the substrate.

In embodiments wherein the method comprises placing the or each supporting member within a holder, the method may further comprise transferring the holder between a series of chambers; wherein each chamber comprises a processing medium for performing the corresponding processing step.

The or each supporting member may comprise a planar form having a front surface, a back surface and at least one edge. In some embodiments the or each supporting member comprises a substantially rectangular form having a front surface, a back surface, a pair of long edges and a pair of short edges. In such embodiments, the method may comprise providing the substrate on either the front surface or the back surface of the or each supporting member and locating the or each supporting member within the electrophoresis tank such that one of the long edges is located substantially parallel with the base of the tank.

The or each supporting member may comprise a slide which is formed from glass or a plastics material, for example.

According to a second aspect of the present invention there is provided an apparatus for performing electrophoretic analysis on a substrate comprising: at least one supporting member having a surface for locating a substrate in use; an electrophoresis tank having a base and side walls enclosing a volume containing an electrophoresis buffer and a means to apply an electric current between ends thereof; and a means to locate the or each supporting member in the tank such that the surface of the or each supporting member upon which the substrate is located, in use, is aligned nonparallel with respect to the base of the electrophoresis tank and is substantially parallel with the direction of the electric current.

The supporting member location means may comprise a holder comprising a slot into which a supporting member may be placed.

In some embodiments there is provided a plurality of supporting members each having a surface for locating a substrate in use.

The location means may comprise a holder comprising a series of slots into which the or each supporting member may be placed in order to align the or each supporting member with respect to the electrophoresis tank and the electric current.

The holder may be dimensioned such that the surface of the or each supporting member upon which the substrate is located is substantially perpendicular to the base of the electrophoresis tank when the holder is located within the tank.

In some embodiments there is provided more than one holder. In such embodiments the electrophoresis tank may be dimensioned such that more than one holder can be located therein.

The or each holder and the electrophoresis tank may be dimensioned to allow at least 5, at least 10, at least 15, at least 20, at least 25, at least 50, at least 75, at least 100, or at least 150 supporting members to be located within the electrophoresis tank at any one time.

The or each holder may be removable from within the electrophoresis tank.

The or each holder may further comprise a handle.

In some embodiments the apparatus further comprises at least one chamber having contained therein a processing medium for performing a desired pre or post electrophoresis processing step. The at least one chamber may be operable to receive at least one of the or each holder such that the or each supporting member need not be removed from within the or each holder whilst performing the or each processing step.

The electrophoresis tank may comprise a first end and a second end. In some embodiments the electric current is induced between the first end and the second end. In such embodiments the electrophoresis tank may comprise an electrode at each end operable to induce the electric current between the two ends of the tank.

In embodiments wherein the electrophoresis tank comprises a first end and a second end, the or each holder and/or the or each supporting member may extend in a direction from one of the first end or the second end to the other of the first end of the second end.

There may be an array of holders, such as a 2×2 array, a 3×3 array or the like, for example.

In some embodiments the or each supporting member may comprise a slide, which may be a glass slide, for example. The glass slide may be a microscope-slide.

According to a third aspect of the present invention there is provided a method in accordance with the first aspect of the present invention using the apparatus of the second aspect of the present invention comprising the steps of: providing a substrate on a surface of at least one supporting member; and performing electrophoresis on the substrate by submerging the or each supporting member in an electrophoresis tank having a base and side walls enclosing a volume containing an electrophoresis buffer and inducing an electric current between ends thereof; wherein the or each supporting member is aligned within the tank such that each surface upon which the substrate is located is nonparallel with respect to the base of the electrophoresis tank and is substantially parallel to the direction of the electric current.

The method may comprise placing the or each supporting member within a holder which is operable in use to retain the or each supporting member in the correct alignment with respect to the electrophoresis tank.

DETAILED DESCRIPTION OF THE INVENTION

In order that the invention may be more clearly understood embodiments thereof will now be described, by way of example only, with reference to the accompanying drawings, of which:

A prior art method of performing gel electrophoresis will now be described with reference to FIG. 1.

Initially cells are suspended in a low melting point agarose (step I). The agarose gel containing the cells is then dispensed onto a microscope slide which has been previously coated with agarose having a normal melting point (step II). Subsequently, the slides are left overnight in an ice-cold lysis buffer (step III). The lysis buffer is typically 100 mM disodium EDTA, 2.5 M NaCl, 10 mM Tris-HCl, pH 10, containing 1% triton X-100. The slides are then washed in distilled water (step IV).

In particular applications of singe cell gel electrophoresis, such as for alkaline and enzyme-modified comet assay, the slides may be immersed in an enzyme digestion buffer at this point. Typical enzyme digestion buffers used include 40 mM HEPES, 0.1 M KCl, 0.5 mM EDTA and 0.2 mg/mL BSA (pH 8.0). Further steps such as incubation may also be performed at this stage.

Once fully prepared, the slides are placed within an electrophoresis tank (step V). The electrophoresis tank has a base and side walls enclosing a volume. In step (V) of FIG. 1, the electrophoresis tank is shown to have a raised portion of the base onto which the slides are placed. This is to prevent the slides from contacting the electrodes, which are typically located within the region adjacent the lower portions of the base. In this method of electrophoresis, the slides are located within the electrophoresis tank horizontally such that the surface of the slide containing the cells is positioned parallel to the base of the tank. The electrophoresis tank is filled with cold alkaline electrophoresis buffer. An example electrophoresis buffer used is 300 mM NaOH, 1 mM disodium EDTA, pH≥13 although buffers with differing pH can be used.

After the slides have been removed from the electrophoresis tank they are drained, neutralised and then washed with distilled water (steps VI to VIII). Following overnight drying (step IX), the slides are rehydrated with distilled water (step X) and then stained (step XI). An example of a staining medium used is 2.5 μg/mL propidium iodide (PI). The slides are subsequently re-washed with distilled water (step XII) before they can be analysed. Analysis may be performed using fluorescence microscopy and suitable software (step XIII).

Figure 2:
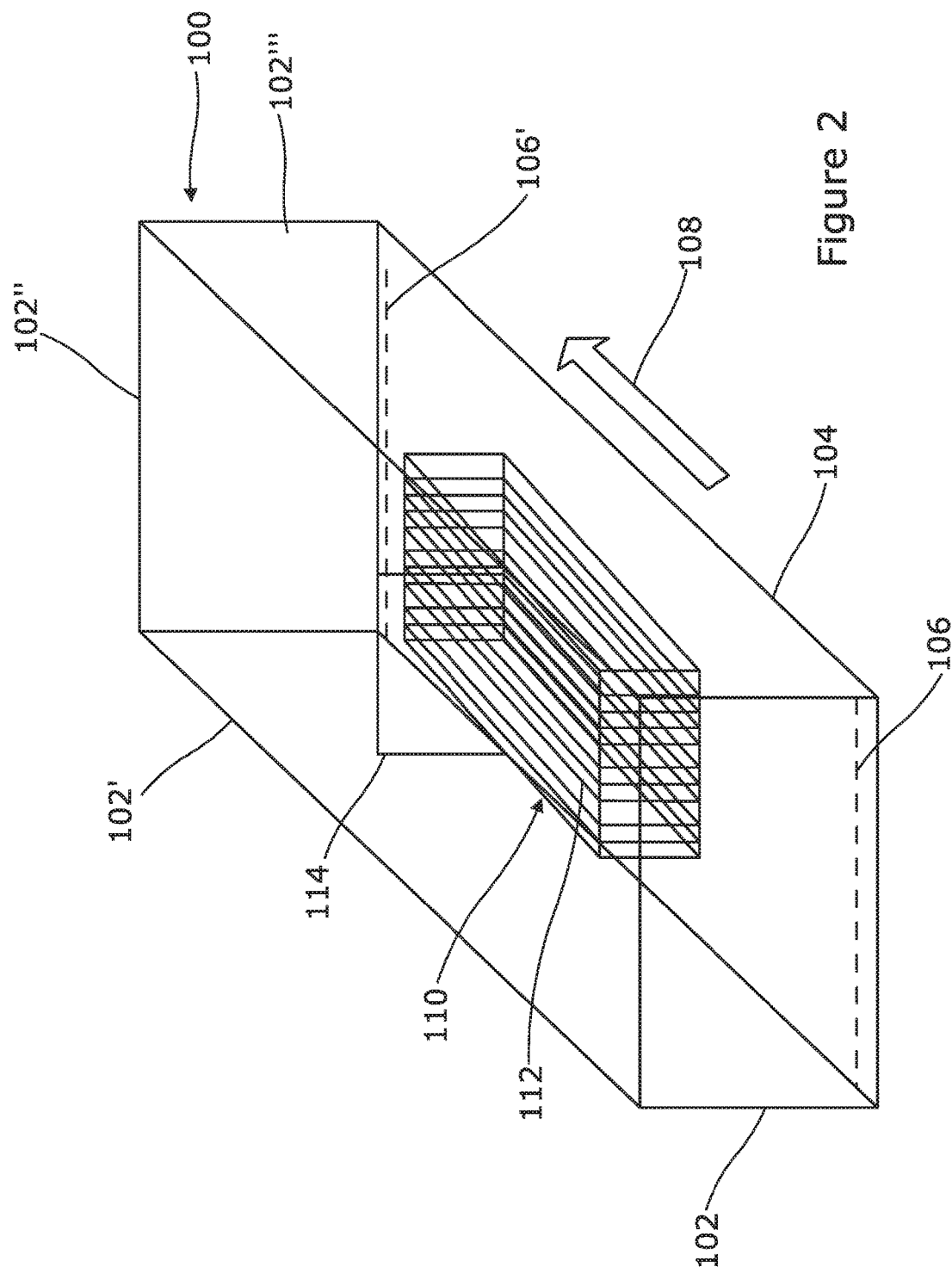
FIG. 2 is a perspective view of an embodiment of an electrophoresis tank and holder in accordance with the present invention.

An embodiment of an electrophoresis tank 100 and a holder 110 in accordance with the present invention is now described with reference to FIG. 2 which are shown in perspective view.

The electrophoresis tank 100 has side walls 102 and a base 104. The tank 100 is cuboidal in shape and has electrodes 106, 106' located at opposing ends. The direction of the electric current between the two electrodes is shown by arrow 108. A supporting member holder in the form of a slide holder 110 is located within the electrophoresis tank 100.

The slide holder 110 has a plurality of slots 112 each operable to receive a slide. When located within the slide holder 110, the slides are orientated such that the largest surface of each slide is substantially perpendicular to the base 104 of the tank 100. The slide holder 110 is also removable from within the tank 100. To assist in the removal of the slide holder 110 from within the tank 100, the holder 110 is provided with a handle 114.

Although in the illustrated embodiment the slide holder 110 has slots 112 which orientate the slides such that the largest surface of each slide is substantially perpendicular to the base 104 of the tank 100, it is envisaged that slide holders 110 may be provided wherein the surfaces of slides are orientated at any suitable angle with respect to the base 104 of the tank 100, providing it is greater than around 5 degrees or 10 degrees.

Figure 3A:
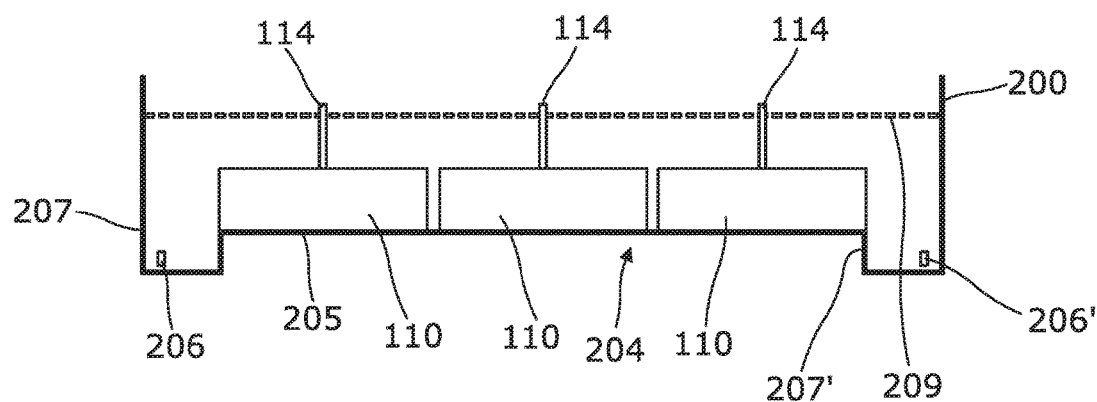
FIG. 3A is a side cross-sectional view of an embodiment of an electrophoresis tank and slide holders of the present invention.
Figure 3B:
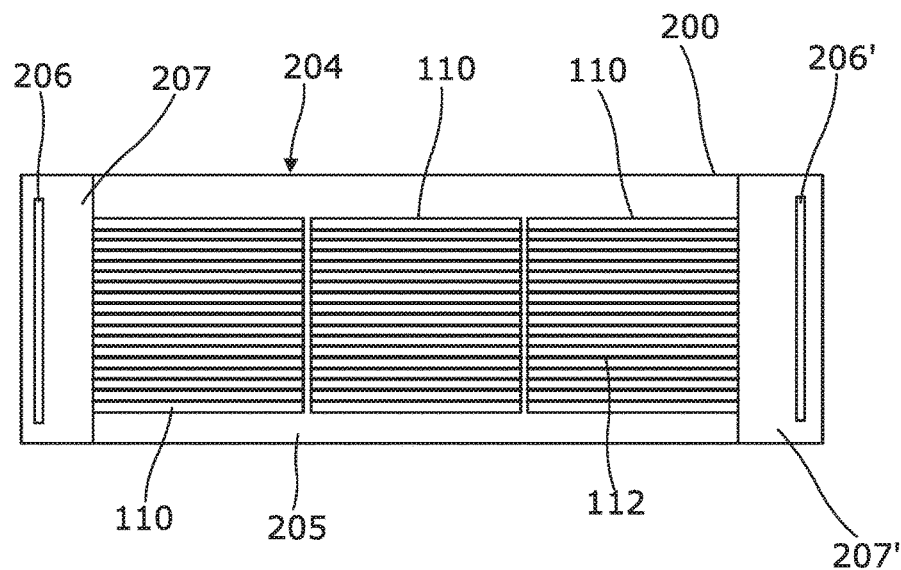
FIG. 3B is a plan view of the electrophoresis tank and slide holders as illustrated in FIG. 3A.

FIGS. 3A and 3B show a side cross-sectional view and a plan view, respectively, of an electrophoresis tank 200 and a plurality of slide holders 110 in accordance with the present invention.

The base 204 of the electrophoresis tank 200 shown in FIGS. 3A and 3B has a raised middle portion 205. Electrodes 206, 206' are positioned within the regions located adjacent the lower portions 207, 20T of the base 204 of the tank 200. The dashed line 209 in FIG. 3A indicates the level of the electrophoresis buffer when the apparatus is in use.

In other tanks, the base may not be raised, which has the advantage of reducing the volume of buffer needed for electrophoresis in the tank.

Located within the electrophoresis tank 200 are slide holders 110. The holders 110 are identical to the slide holder as illustrated in FIG. 2 each having a plurality of slots 112 operable to receive a slide and orientated such that the largest surface of each slide is substantially perpendicular to the base 204 of the tank 200 when located within the holders 110. The slide holders 110 are also removable from within the tank 200 and to assist in the removal of the slide holders 110, each are provided with a handle 114. Each of the slide holders 110 is located on the raised portion 205 of the base 204 of the electrophoresis tank 200 in order to prevent the slides from contacting the electrodes 206, 206'.

A method of performing electrophoresis will now be described with reference to FIGS. 1-4. The method in accordance with the present invention involves substantially the same steps as the method described above with reference to FIG. 1. However, the proposed method involves locating the slides such that the surface upon which the cells are located is orientated nonparallel with the base 104, 204 of the electrophoresis tank 100, 200 during electrophoresis. In the embodiments illustrated in FIGS. 2-4, the slides are located within a slide holder 110 and are orientated such that the surface of the slides upon which the cells are located is substantially perpendicular to the base 104, 204 of the electrophoresis tank 100, 200.

Figure 1:
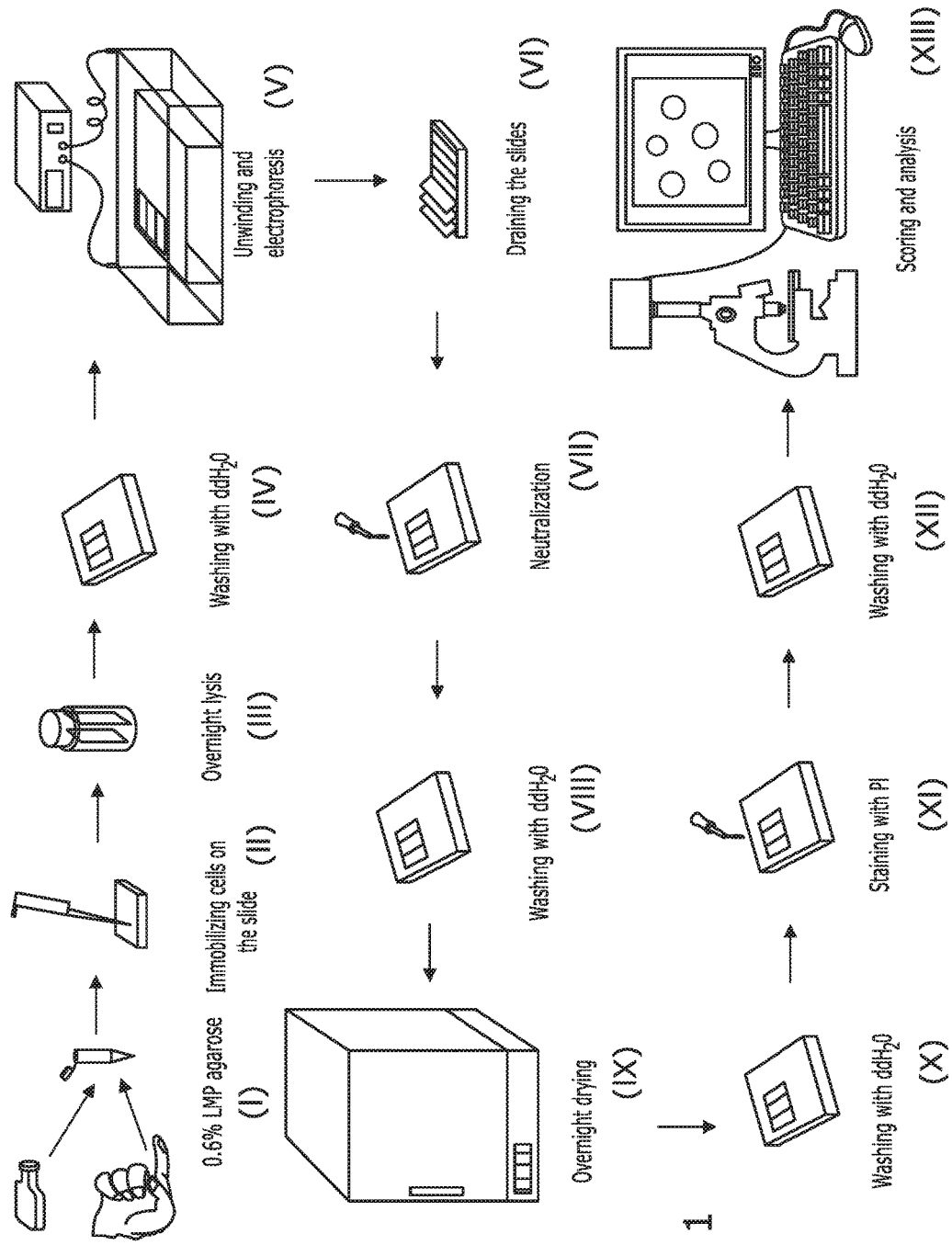
FIG. 1 is a schematic overview of the steps involved in conventional single cell gel electrophoresis.
Figure 4:
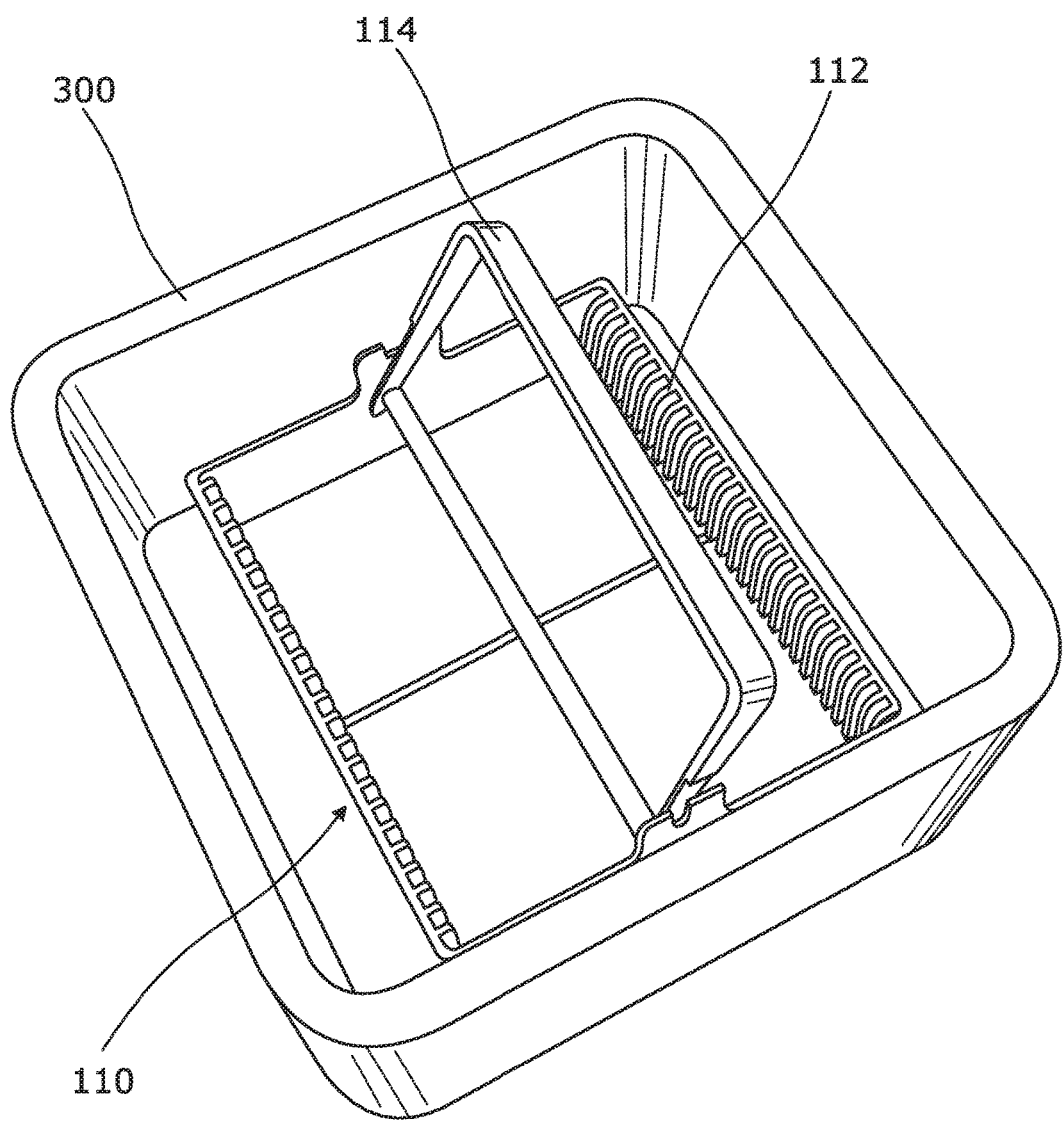
FIG. 4 is a perspective view of an embodiment of a processing chamber and an embodiment of a holder of the present invention.

It is also envisaged that any of steps (II) to (XII), as shown in FIG. 1, may be performed on the cells whilst the slides are located within the holder 110. Furthermore, FIG. 4 illustrates a processing chamber 300 which may be used for any one of steps (III) to (IV), steps (VII) to (VIII) and steps (X) to (XII). The processing chamber 300 defines a volume which is operable to receive a slide holder 110. In use, the processing chamber 300 is filled with the relevant processing medium and the slide holder 110 is submerged within said medium. In this way, the number of cell containing slides able to be processed through each step at any given time is increased. In addition, by retaining the slides in the holder 110 through steps (II) to (XII), the likelihood of the cells becoming damaged or lost is reduced.

Electrophoretic analysis was performed using the prior art method as described with reference to FIG. 1, and the method as discussed with reference to FIGS. 2 to 4. The results of an investigation using both methods is illustrated in FIGS. 5 and 6.

The analysis of the prepared slides involved imaging the slides through fluorescence spectroscopy and using the obtained image to calculate the percentage of the DNA within the 'tail' of the comet (% tail DNA), or other parameters often used in the Comet assay, for example, olive tail moment, or tail length.

Figure 5:
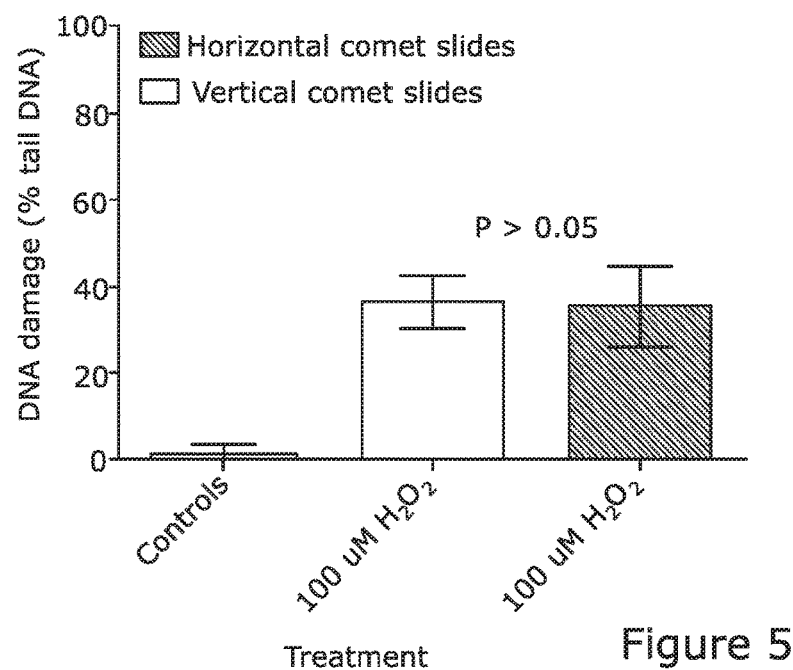
FIG. 5 is a graph illustrating the results obtained using a method of electrophoresis in accordance with the present invention and a prior art method.
Figure 6:
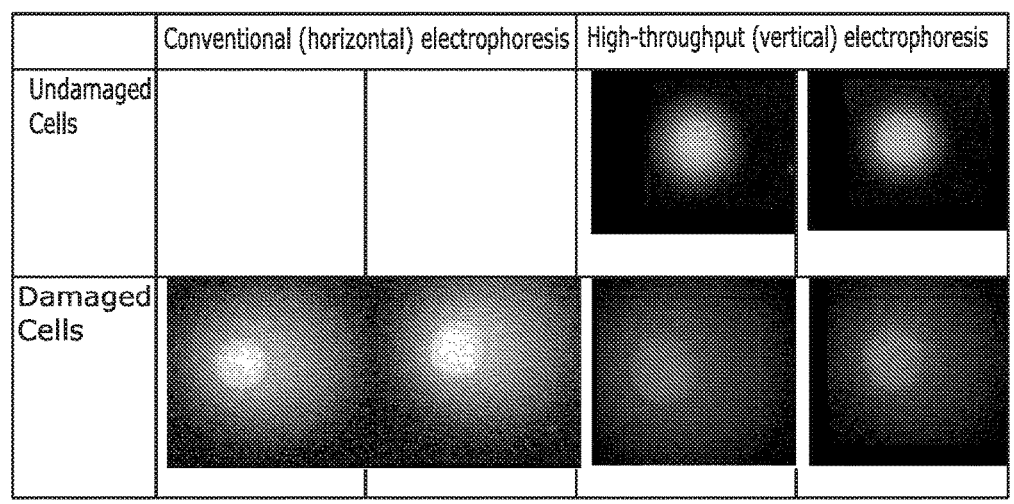
FIG. 6 is a series of images obtained under a microscope showing the results obtained a using a method of electrophoresis in accordance with the present invention and a prior art method.

FIG. 5 shows the percentage of DNA within the tail of the comet after performing electrophoresis using the prior art method, and the method in accordance with the present invention as described above. FIG. 5 also provides data from a control sample. The slides were prepared in the same way and from the same sample of cells for each method, with the exception of the orientation of the slides during the electrophoresis stage. The data labelled horizontal comet slides refers to the results obtained using the prior art method of electrophoresis, and the data labelled vertical comet slides refers to the results obtained using the method in accordance with the present invention.

As can be seen from FIG. 5, the data obtained is similar for both methods of electrophoresis with roughly 40% of the DNA being located within the tail. The control results show approximately 0% of the DNA located within the tail which is to be expected.

FIG. 6 shows images obtained through fluorescence microscopy of both damaged and undamaged cells using both the prior art method (conventional horizontal electrophoresis) and the method in accordance with the present invention (high-throughput vertical electrophoresis). The images show no substantial difference between the results obtained by each method and this is confirmed by the data illustrated in FIG. 5.

As illustrated in FIGS. 5 and 6, the method in accordance with the present invention returns similar results to prior art methods whilst simultaneously providing an increase in the number of cell containing slides being processed at any given time.

The above embodiments are described by way of example only. Many variations are possible without departing from the scope of the invention as defined in the appended claims.

The invention claimed is:

1. A method of performing electrophoretic analysis on a substrate comprising:
   providing the substrate on a support surface of at least one supporting member, the support surface adapted to receive the substrate so as to provide an exposed, external substrate surface opposite at least a portion of the support surface, wherein the or each supporting member comprises a slide; and
   performing electrophoresis on the substrate by submerging the or each supporting member in an electrophoresis tank having a base and side walls enclosing a volume containing a single electrophoresis buffer for contacting the external substrate surface on the support surface of the or each supporting member and inducing an electric current between ends thereof;
   wherein the or each supporting member is aligned within the electrophoresis tank, in one of a plurality of slots for retaining an individual supporting member, such that each support surface of the at least one supporting member upon which the substrate is located is substantially perpendicular to the base of the electrophoresis tank and is substantially parallel with the direction of the electric current, and wherein the external substrate surface is exposed to the electrophoresis buffer.

2. The method of claim 1 wherein the method comprises providing a holder and placing the or each supporting member in the holder in order to retain the or each supporting member in the correct alignment with respect to the electrophoresis tank.

3. The method of claim 2 wherein the holder comprises a plurality of compartments for holding a plurality of supporting members.

4. The method of claim 2 wherein the or each supporting member is placed within a holder which is removable from within the electrophoresis tank.

5. The method according to claim 1 further comprising performing pre-electrophoresis processing steps prior to performing electrophoresis on the substrate.

6. The method of claim 1 further comprising performing post-electrophoresis processing steps after performing electrophoresis on the substrate.

7. The method of claim 4 comprising transferring the holder between a series of chambers; wherein each chamber comprises a processing medium for performing a pre or post electrophoresis processing step.

8. The method of claim 1 wherein the electrophoretic analysis comprises performing single cell gel electrophoresis.

9. The method according to claim 1 wherein the method comprises providing the substrate on the support surface of a plurality of supporting members; and performing electrophoretic analysis on the substrate located on the support surface of a plurality of supporting members.

10. The method as claimed in claim 1 wherein the or each slide comprises a glass slide.

11. An apparatus for performing electrophoretic analysis on a substrate comprising:
    at least one supporting member having a support surface for locating the substrate in use, the support surface adapted to receive the substrate so as to provide an exposed, external substrate surface opposite at least a portion of the support surface, wherein the or each supporting member comprises a slide;
    an electrophoresis tank having a base and side walls enclosing a volume containing a single electrophoresis buffer for contacting the external substrate surface on the support surface of the or each supporting member and a means to induce an electric current between ends thereof;
    and at least a holder for locating the or each supporting member within the electrophoresis tank in one of a plurality of slots for retaining an individual supporting member, such that the support surface of each supporting member upon which the substrate is located, in use, is substantially perpendicular to the base of the electrophoresis tank and is substantially parallel with the direction of the electric current, and wherein the external substrate surface is exposed to the electrophoresis buffer.

12. The apparatus of claim 11 wherein the holder comprises a slot into which a supporting member may be placed.

13. The apparatus of claim 11 wherein the holder comprises a series of slots into which the or each supporting member may be placed in order to align the or each supporting member with respect to the electrophoresis tank and the electric current.

14. The apparatus of claim 12 wherein there is more than one holder and the electrophoresis tank is dimensioned such that more than one holder can be located therein.

15. The apparatus of claim 12 wherein the holder is removable from within the electrophoresis tank.

16. The apparatus according to claim 11 further comprising at least one chamber having contained therein a processing medium for performing a desired pre or post electrophoresis processing step.

17. The apparatus of claim 16 wherein the at least one chamber is operable to receive the holder such that the slide need not be removed from within the holder whilst performing the or each processing step.

18. The apparatus of claim 11 wherein there is provided a plurality of supporting members each having a support surface for locating the substrate in use.

19. The apparatus of claim 11 wherein the or each slide comprises a glass slide.

\* \* \* \* \*